(12) United States Patent
Omori et al.

(10) Patent No.: US 8,246,608 B2
(45) Date of Patent: Aug. 21, 2012

(54) MEDICAL MANIPULATOR SYSTEM

(75) Inventors: Shigeru Omori, Ashigarakami-gun (JP);
Masaru Nagashimada, Fujinomiya (JP);
Makoto Jinno, Ota-ku (JP); Takamitsu Sunaoshi, Yokohama (JP)

(73) Assignees: Terumo Kabushiki Kaisha, Tokyo (JP);
Kabushiki Kaisha Toshiba, Tokyo (JP)

( * ) Notice: Subject to any disclaimer, the term of this patent is extended or adjusted under 35 U.S.C. 154(b) by 1027 days.

(21) Appl. No.: 12/201,065

(22) Filed: Aug. 29, 2008

(65) Prior Publication Data

US 2009/0062814 A1    Mar. 5, 2009

(30) Foreign Application Priority Data

Aug. 31, 2007   (JP) ................................ 2007-227010

(51) Int. Cl.
*A61B 17/94*    (2006.01)
*A61B 19/00*    (2006.01)

(52) U.S. Cl. ........................................... 606/1; 606/130

(58) Field of Classification Search ................ 606/1, 130
See application file for complete search history.

(56) References Cited

U.S. PATENT DOCUMENTS

| | | | |
|---|---|---|---|
| 6,331,181 B1 | 12/2001 | Tierney et al. | |
| 7,314,473 B2 | 1/2008 | Jinno et al. | |
| 8,157,793 B2* | 4/2012 | Omori et al. | 606/1 |
| 2004/0133189 A1 | 7/2004 | Sakurai | |
| 2006/0079865 A1* | 4/2006 | Jinno et al. | 606/1 |
| 2008/0015611 A1* | 1/2008 | Jinno et al. | 606/130 |
| 2008/0103491 A1* | 5/2008 | Omori et al. | 606/1 |
| 2009/0030428 A1* | 1/2009 | Omori et al. | 606/130 |
| 2009/0036901 A1* | 2/2009 | Omori | 606/130 |

FOREIGN PATENT DOCUMENTS

| | | |
|---|---|---|
| JP | 2004-105451 | 4/2004 |
| JP | 2004-208922 | 7/2004 |

\* cited by examiner

*Primary Examiner* — Henry M Johnson, III
(74) *Attorney, Agent, or Firm* — Oblon, Spivak, McClelland, Maier & Neustadt, L.L.P.

(57) ABSTRACT

A medical manipulator system includes a manipulator, an operating unit for entering operation commands, motors for actuating a working unit, and a controller for energizing the motors based on operation commands supplied from the operating unit. When an activation resetting switch and a resetting switch are operated according to a predetermined procedure, the controller performs a resetting process to return the motors to an origin. The controller is capable of controlling three manipulators. The activation resetting switch is shared by the three manipulators, and there are three resetting switches corresponding to the three manipulators.

7 Claims, 11 Drawing Sheets

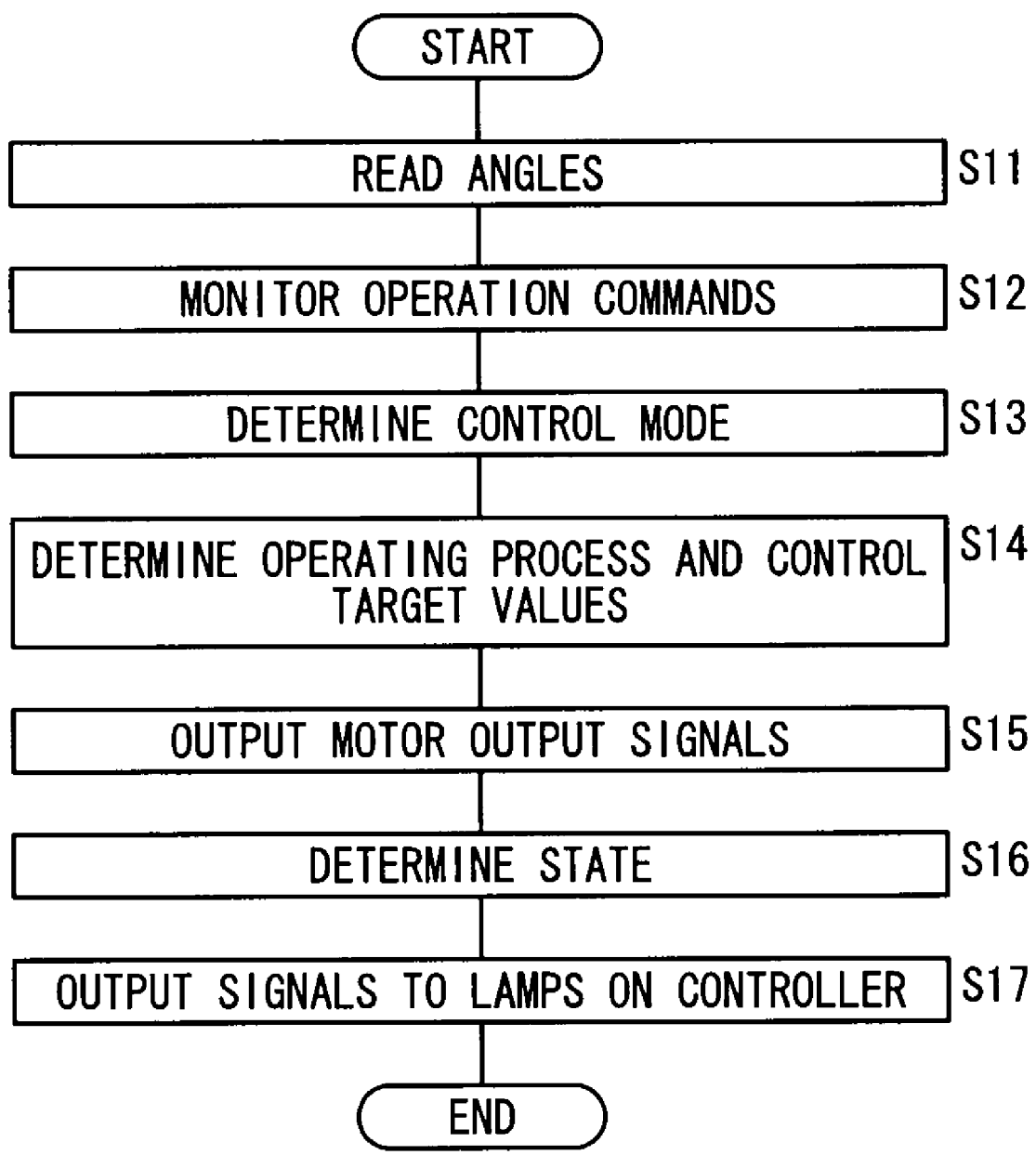

MEDICAL MANIPULATOR SYSTEM

BACKGROUND OF THE INVENTION

1. Field of the Invention

The present invention relates to a medical manipulator system including a working unit which is operable on the basis of an operation command input from an operating unit.

2. Description of the Related Art

In laparoscopic surgery, a number of small holes are opened in a patient's abdomen or the like, and an endoscope, a forceps (or manipulator) or the like is inserted, and surgery is carried out while the surgeon observes an image from the endoscope on a monitor. In this type of laparoscopic surgery, owing to the fact that opening of the abdominal cavity is unnecessary, the burden on the patient is small, and the number of days required for the post-operative recovery and the number of days spent in the hospital can be significantly reduced. Therefore, laparoscopic surgical operations are expected to find an increased range of applications.

As disclosed in JP 2004-105451 A, for example, a manipulator system comprises a manipulator and a controller for controlling the manipulator. The manipulator comprises an operating unit which is manually operable and a working unit replaceably mounted on the operating unit.

The working unit (instrument) comprises a long joint shaft and a distal-end working unit (also referred to as an end effector) mounted on the distal end of the joint shaft. The operating unit has actuators (motors) for actuating the working unit at the distal end through wires. The wires are wound around respective pulleys disposed in a proximal end portion of the working unit. The controller energizes the motors of the operating unit to cause the pulleys to move the wires back and forth.

The working unit does not include electronic devices such as sensors or the like because it should easily be cleaned and sterilized, and is incapable of directly detecting the positions or origins of the pulleys disposed in the distal-end working unit and the rear end of the working unit. The axis positions of the distal-end working unit are calculated based on respective angular displacements of the motors.

Various different working units, including a gripper, scissors, an electrosurgical knife, an ultrasonic knife, a medical drill, etc., are used to perform respective surgical techniques in a laparoscopic surgical operation process. These working units are detachably mounted on the operating unit. When the working units are selectively mounted on the operating unit, the pulleys in the proximal end of the working unit are held in engagement with the rotational shafts of the motors in the operating unit.

In a system where different working units are selectively connected to one operating unit, it is necessary to establish a motor phase which serves as a common axis position for allowing all the working units to be detachably mounted on the operating unit (see, for example, JP 2004-105451 A). The established motor phase is referred to as an origin or initial position.

If the distal-end working unit is to be replaced with another distal-end working unit, then the manipulator itself may be replaced. In this case, the connector of the manipulator which connects the operating unit to the controller is disconnected from the controller, and the connector of the other manipulator is connected to the controller.

In general industrial manipulator systems, the manipulator and the controller keep connected to each other while in operation. However, medical manipulator systems should preferably have the manipulator easily separable from the controller because different types of working units are selectively used, as described above.

Manipulator systems of the related art are disclosed in JP 2004-105451 A, JP 2004-208922 A, and U.S. Pat. No. 6,331,181.

According to JP 2004-105451 A, there have been proposed arrangements which make it unnecessary to take into account motor coil excitation switchover upon installation and removal of the working unit and also electric configurations.

JP 2004-208922 A discloses electric installation and removal of a plurality of distal-end tools (working units).

U.S. Pat. No. 6,331,181 discloses a medical manipulator system including a circuit for acquiring ID, on a manipulator on the distal end. A controller acquires the ID information and controls installation and removal of the manipulator based on the acquired ID information.

As described above, the axis position of the distal-end working unit is calculated on the basis of the origin. If the working unit is to be replaced with another working unit during a surgical process, then the other working unit to be newly mounted on the operating unit needs to be in an axis position that is exactly held in alignment with the origin. Stated otherwise, when the working unit is removed from the operating unit, the working unit should preferably be in an axis position aligned with the origin.

If the working unit is removed while the motors are being angularly displaced from the origin for some reasons, then it may be necessary for the operator to perform a resetting process to forcibly return the motors to the origin. However, since the resetting process is a forcible process that is not performed normally, it should not be activated carelessly.

SUMMARY OF THE INVENTION

It is one of the objects of the present invention to provide a medical manipulator system which is capable of appropriately controlling a resetting process for actuators.

A medical manipulator system according to one aspect of the present invention includes a manipulator, a controller connected to the manipulator, and a first resetting switch and a second resetting switch. The manipulator includes an operating unit having an actuator, a grip handle for being gripped by a human hand, and an input unit for inputting an operation command, a working unit removably mounted on the actuator and having a shaft and a distal-end working unit mounted on a distal end of the shaft, the distal-end working unit being angularly movable about a pivot axis not parallel to the axis of the shaft in response to operation of the actuator, and a working unit detecting unit for supplying the controller with a signal indicating whether the working unit is present on the operating unit or not, wherein when the working unit is removed from the operating unit and when the actuator is not at an origin, the controller produces a warning, and performs a resetting process to return the actuator to the origin if both of the first resetting switch and the second resetting switch are operated according to a predetermined procedure.

Since the resetting process is performed if the first resetting switch and the second resetting switch are operated according to the predetermined procedure, the resetting process is not activated carelessly.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 11 is a main flowchart of an operation sequence of the medical manipulator system.

DESCRIPTION OF THE PREFERRED EMBODIMENT

A medical manipulator system 500 according to an embodiment of the present invention will be described below with reference to FIGS. 1 through 11. The medical manipulator system 500 (see FIG. 1) is used in a laparoscopic surgical operation process or the like.

Figure 1:
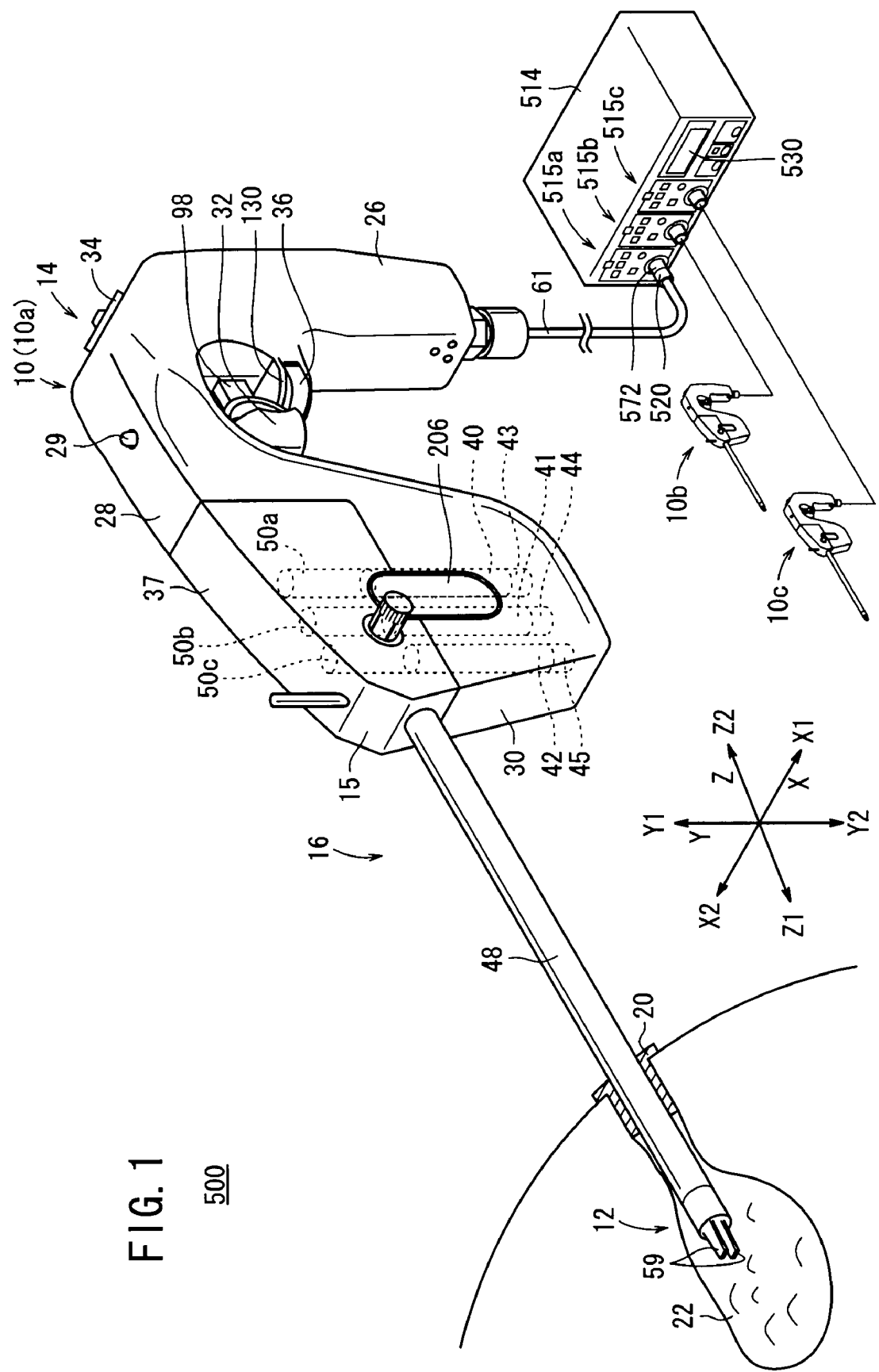
FIG. 1 is a perspective view of a medical manipulator system according to an embodiment of the present invention.

As shown in FIG. 1, the medical manipulator system 500 comprises a manipulator 10 and a controller 514.

The manipulator 10 and the controller 514 are detachably connected to each other by a connector 520.

The manipulator 10 has a distal-end working unit 12 for gripping a portion of a living tissue, a curved needle, or the like for performing a certain surgical treatment. The manipulator 10 comprises an operating unit 14 and a working unit 16 as basic components. The controller 514 electrically controls the manipulator 10, and is connected by a connector 520 to a cable 61 extending from the lower end of a grip handle 26 of the operating unit 14.

The controller 514 is capable of independently controlling three manipulators 10 at the same time. The controller 514 has a first port 515a, a second port 515b, and a third port 515c for controlling the first, second, and third manipulators 10, respectively. The first, second, and third manipulators 10 that are connected respectively to the first, second, and third ports 515a, 515b, 515c for being controlled thereby are also referred to as manipulators 10a, 10b, 10c, respectively (see FIG. 1).

Figure 2:
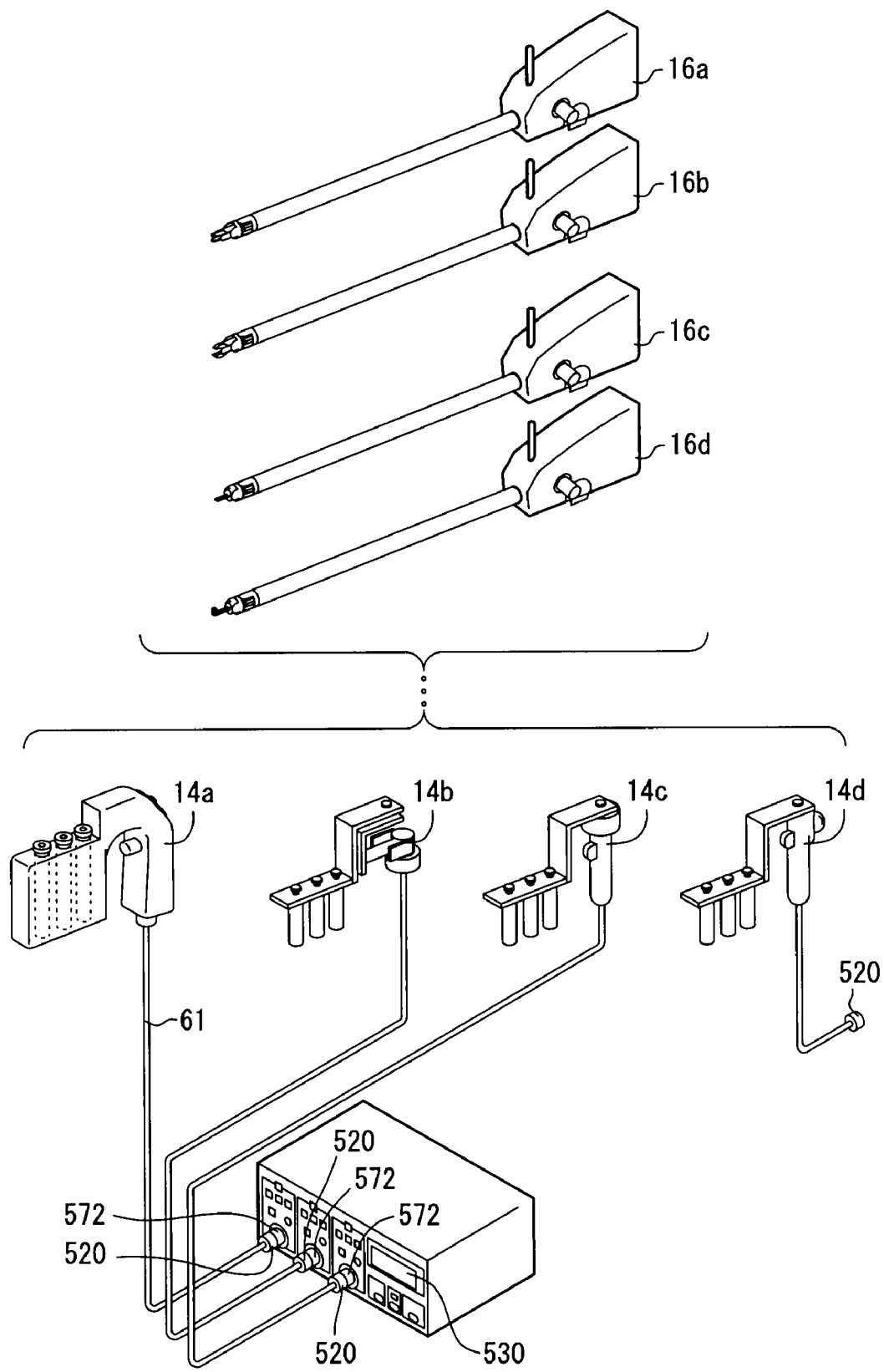
FIG. 2 is a perspective view showing possible combinations of the medical manipulator system according to the embodiment of the present invention.

As shown in FIG. 2, the manipulator system 500 may selectively have various configurations. Specifically, operating units 14a, 14b, 14c, 14d are available as variations for the operating unit 14, and working units 16a, 16b, 16c, 16d are available as variations for the working unit 16.

The operating units 14a, 14b, 14c, 14d can selectively be connected to the controller 514, and the working units 16a, 16b, 16c, 16d can selectively be mounted on a selected one of the operating units 14a, 14b, 14c, 14d. A surgeon who handles the medical manipulator system 500 can selectively combine the operating units 14a, 14b, 14c, 14d and the working units 16a, 16b, 16c, 16d depending on the surgical procedure which the surgeon is going to perform and the degree to which the surgeon is familiar with those operating and working units. The working unit 16b has scissors as its distal-end working unit 12. The working unit 16c has a blade-like electrosurgical knife as its distal-end working unit 12. The working unit 16d has a hook-like electrosurgical knife as its distal-end working unit 12. The working units 16a, 16b, 16c, 16d have common pulleys 50a, 50b, 50c (see FIG. 1) in connectors 15 thereof.

Since the controller 514 is capable of independently controlling three manipulators 10 at the same time as described above, three of the operating units 14a, 14b, 14c, 14d can be connected to the first port 515a, the second port 515b, and the third port 515c.

The manipulator 10 which comprises the operating unit 14 and the working unit 16 will be described below.

The distal-end working unit 12 of the manipulator 10 serves to grip a portion of a living tissue, a curved needle, or the like for performing a certain surgical treatment, and is usually referred to as gripping forceps or a needle driver (needle holder).

Figure 3:
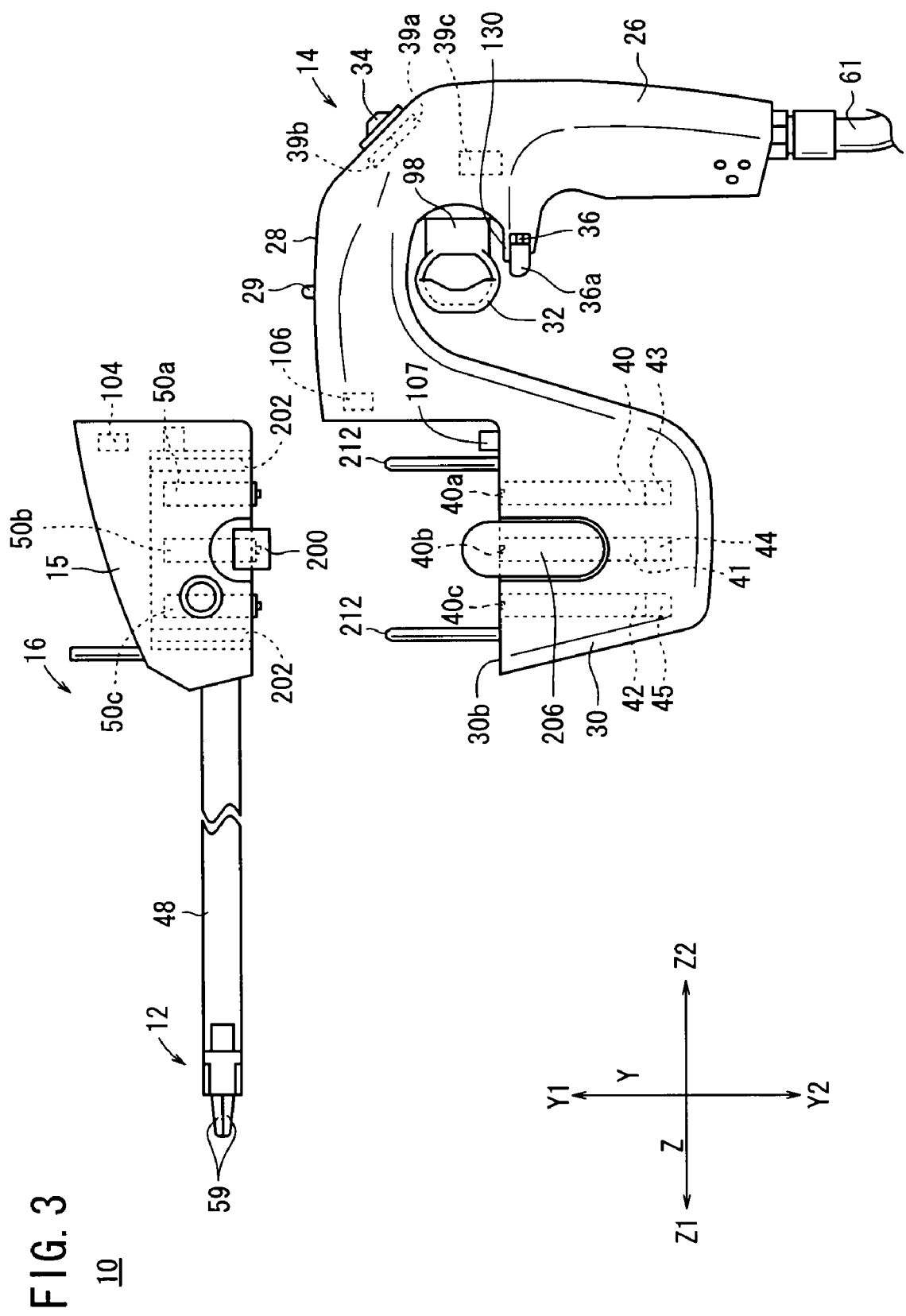
FIG. 3 is a side elevational view of a manipulator of the medical manipulator system with a working unit and an operating unit being separate from each other.

As shown in FIGS. 1 and 3, the manipulator 10 includes the operating unit 14 which is held and operated by hand and the working unit 16 detachably mounted on the operating unit 14.

It is assumed in the description which follows that transverse directions in FIG. 1 are referred to as X directions, vertical directions as Y directions, and longitudinal directions of a hollow joint shaft 48 as Z directions. Of the X directions, the rightward direction as viewed from the distal end is referred to as an X1 direction, and the leftward direction as an X2 direction. Of the directions, the upward direction is referred to as a Y1 direction, and the downward direction as a Y2 direction. Of the Z directions, the forward direction is referred to as a Z1 direction, and the rearward direction as a Z2 direction. Unless otherwise noted, these directions represent directions of the manipulator 10 when it is of a neutral attitude. The definition of the above directions is for illustrative purpose only, and the manipulator 10 can be used in any orientations, e.g., it may be used upside down.

The working unit 16 includes the distal-end working unit 12 for performing working operation, a connector 15 connected to an actuator block (actuator) 30 of the operating unit 14, and an elongate hollow joint shaft 48 coupling the distal-end working unit 12 and the connector 15 to each other. When a predetermined action is performed on the actuator block 30, the working unit 16 can be separated from the operating unit 14, so that the working unit 16 can be cleaned, sterilized, and serviced for maintenance.

The distal-end working unit 12 and the joint shaft 48, which are small in diameter, can be inserted into a body cavity 22 through a trocar 20 in the form of a hollow cylinder mounted in an abdominal region or the like of the patient. The distal-end working unit 12 is actuated by the operating unit 14 to perform various surgical techniques to remove, grip, suture, or ligate (tie-knot) an affected part of the patient's body in the body cavity 22.

The operating unit 14 includes a grip handle 26 gripped by hand, a bridge 28 extending from an upper portion of the grip handle 26, and an actuator block 30 connected to a distal end of the bridge 28.

As shown in FIG. 1, the grip handle 26 of the operating unit 14 extends in the Y2 direction from the end of the bridge 28, and has a length suitable for being gripped by a human hand. The grip handle 26 has a trigger lever 32 as an input means, a composite input unit 34, and a switch 36.

The bridge 28 has an LED (indicator) 29 in an easily visually recognizable position on an upper or side surface thereof. The LED 29 is an indicator for indicating a controlled state of the manipulator 10. The LED 29 is of a size large enough to be easily visually recognizable by the operator, and yet is sufficiently small and light not to interfere with the operation of the manipulator 10. The LED 29 is located in a visually recognizable position substantially centrally on the upper surface of the bridge 28.

A cable 61 has an end connected to the lower end of the grip handle 26 and an opposite end connected to the controller 514. The grip handle 26 and the cable 61 are integrally connected to each other. The grip handle 26 and the cable 61 may be connected to each other by a connector.

The composite input unit 34 serves as a composite input means for giving rotational commands in rolling directions (shaft rotating directions) and yawing directions (left and right directions) to the distal-end working unit 12. For example, the composite input unit 34 may serve as a first input means movable in the shaft rotating directions for entering commands in the rolling directions and a second input means movable in the left and right directions for entering commands in the yawing directions. The trigger lever 32 serves as an input means for giving opening and closing commands to a gripper 59 (see FIG. 1) of the distal-end working unit 12. The controller 514 holds internal signals indicative of angles of the motors 40, 41, 42 corresponding to a roll axis, a yaw axis, and a gripper axis. On the basis of signals from the composite input unit 34 and the trigger lever 32, the controller 514 changes these internal signals to equalize the angles of the motors 40, 41, 42.

The switch 36 serves as an input means for selectively enabling and disabling the manipulator 10.

Figure 4:
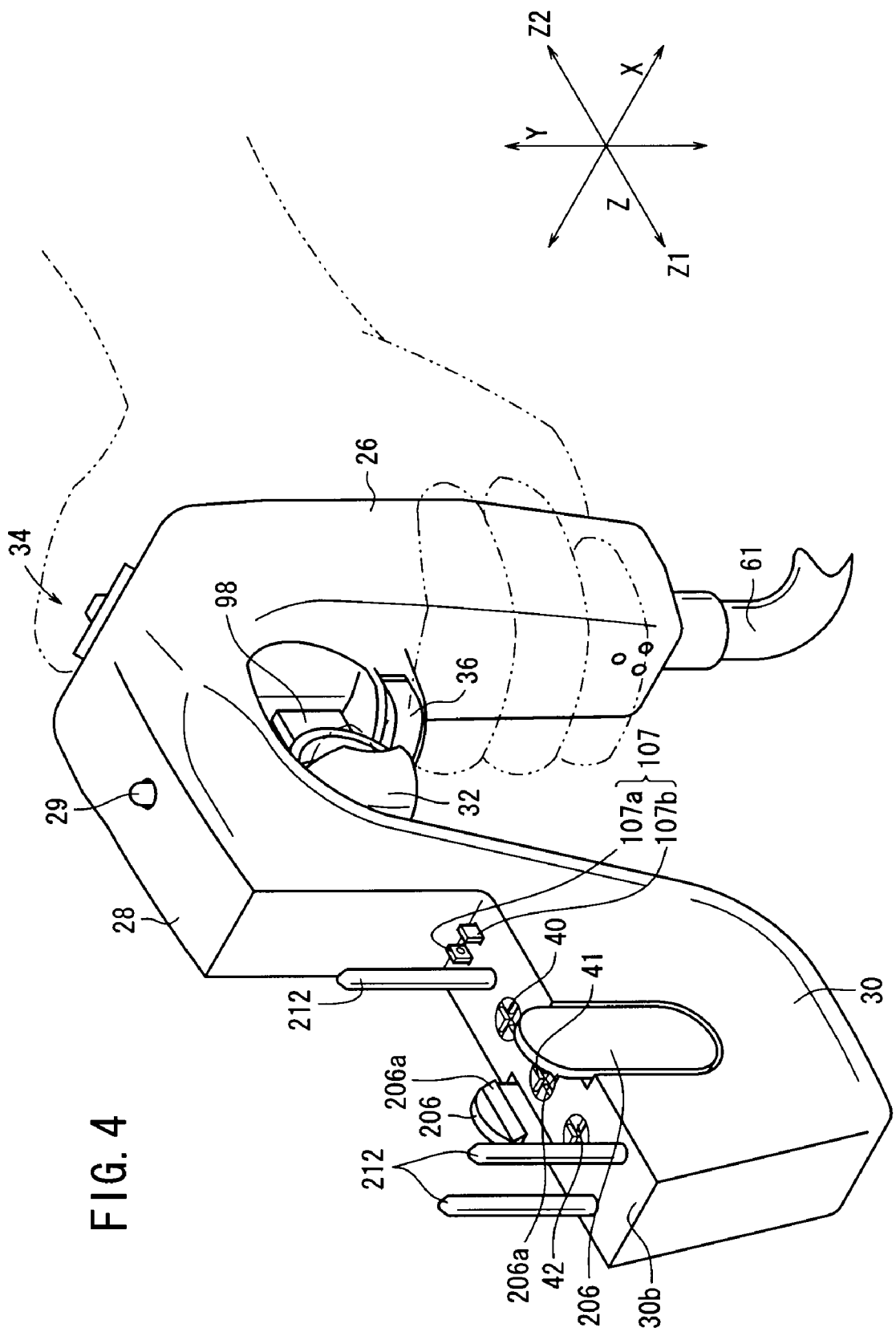
FIG. 4 is a perspective view of the operating unit.

As shown in FIGS. 3 and 4, the composite input unit 34 and the trigger lever 32 are associated with input sensors 39a, 39b, 39c for detecting operational quantities. The input sensors 39a, 39b, 39c supply the detected operational signals to the controller 514. The signals from the input sensors 39a, 39b, 39c are analog signals, for example. Specifically, the input sensors 39a, 39b, 39c generate analog signals ranging from 0.5 V to 4.5 V with respect to an applied voltage of 5 V, and supply the generated analog signals to the controller 514. The signals from the input sensors 39a, 39b, 39c are supplied via a pull-up circuit or a pull-down circuit to the controller 514. The controller 514 can detect whether the connector 520 is connected thereto or disconnected therefrom based on a change in the signals (operation commands) from the input sensors 39a, 39b, 39c. Specifically, when the connector 520 is disconnected, the voltage of the signals from the input sensors 39a, 39b, 39c is brought to 0 V or 5 V by the pull-up circuit or the pull-down circuit. Therefore, the controller 514 detects the disconnection of the connector 520.

The trigger lever 32 is disposed slightly below the bridge 28 and projects in the Z1 direction. The trigger lever 32 is disposed in a position where it can easily be operated by the index finger of the hand that is gripping the grip handle 26.

The trigger lever 32 is operatively coupled to the grip handle 26 by an arm 98, and is movable toward and away from the grip handle 26.

The switch 36 serves as an operating mechanism movable toward and away from the grip handle 26. The trigger lever 32 and the switch 36 are disposed on a surface of the grip handle 26 on the Z1 direction side and are present closely together, i.e., juxtaposed in the longitudinal directions (Y directions) of the grip handle 26. The switch 36 is disposed directly below the trigger lever 32 in the Y2 direction with a thin plate 130 interposed between the switch 36 and the trigger lever 32. The thin plate 130 extends from the grip handle 26 in the Z1 direction.

The switch 36 comprises an alternate switch having a trigger knob 36a. The switch 36 operates as follows: When the trigger knob 36a is pushed toward the grip handle 26 in the Z2 direction, the switch 36 is locked in an ON state, and the trigger knob 36a is held in a position near the grip handle 26. When the trigger knob 36a is pushed again toward the grip handle 26, the switch 36 is released from the ON state into an OFF state. The trigger knob 36a is automatically returned in the Z1 direction to a position remote from the grip handle 26 under the bias of an elastic member, not shown. When the switch 36 is repeatedly operated in this manner, it is automatically held in either the ON state or the OFF state, and the operator does not need to hold the trigger knob 36a pushed in order to hold the switch 36 in either the ON state or the OFF state. The operator may operate the switch 36 only when it is to switch between the ON state and the OFF state. When the operator does not operate the switch 36, the operator can operate the trigger lever 32. Accordingly, the switch 36 and the trigger lever 32 may be present closely together.

The trigger knob 36a projects to different positions when the switch 36 is in the ON state and the OFF state. Therefore, the operator can easily confirm the ON state and the OFF state of the switch 36 by seeing or feeling the trigger knob 36a.

The switch 36 serves to change modes of the manipulator 10. The modes are indicated by the LED 29 and port number lamps 560 (see FIG. 7) to be described later. Specifically, when the manipulator 10 is in an operation mode, the LED 29 and the port number lamps 560 are energized to emit green light continuously, and when the manipulator 10 is in a stop mode, the LED 29 and the port number lamps 560 are de-energized. When the manipulator 10 is in an automatic origin return process and a resetting process, the LED 29 and the port number lamps 560 emit blinking green light. When the manipulator 10 generates an alarm, the LED 29 and the port number lamps 560 emit blinking red light.

The above modes and processes are changed by the switch 36. Specifically, the controller 514, which reads the states of the switch 36, places the manipulator 10 in the operation mode when the switch 36 is in the ON state, operates the manipulator 10 in the automatic origin return process to return the motors 40, 41, 42 to the origin when the switch 36 changes from the ON state to the OFF state, and places the manipulator 10 in the stop mode after the motors 40, 41, 42 are returned to the origin.

The operation mode is a mode in which the operation commands of the operating unit 14 are validated to energize the motors 40, 41, 42. The stop mode is a mode in which the motors 40, 41, 42 are de-energized regardless of whether there are operation commands of the operating unit 14 or not. The resetting process is a process for automatically returning the motors 40, 41, 42 to the origin when a certain action, to be described later, is made. The automatic origin return process and the resetting process are classified as an automatic mode because the motors 40, 41, 42 are operated regardless of whether there are operation commands of the operating unit 14 or not.

The controller 514 distinguishes the above modes and processes from each other and changes the energized states of the LED 29 and the port number lamps 560 based on the distinguished modes and processes.

The actuator block 30 houses therein the motors 40, 41, 42 associated respectively with mechanisms having three degrees of freedom in the distal-end working unit 12. The motors 40, 41, 42 are juxtaposed along the direction in which the joint shaft 48 extends. The motors 40, 41, 42 are small in size and diameter, and the actuator block 30 which houses the motors 40, 41, 42 therein is of a flat compact shape. The actuator block 30 is disposed below an end of the operating unit 14 in the Z1 direction. The motors 40, 41, 42 are energized under the control of the controller 514 based on actions made by the operator on the operating unit 14.

The motors 40, 41, 42 are combined with respective angle sensors 43, 44, 45 for detecting respective angular displacements of the motors 40, 41, 42. The angle sensors 43, 44, 45 supply the detected angle signals to the controller 514. The angle sensors 43, 44, 45 may comprise rotary encoders, for example.

The working unit 16 includes the connector 15 connected to the actuator block 30 and the hollow joint shaft 48 extending from the connector 15 in the Z1 direction. The connector 15 houses pulleys 50a, 50b, 50c rotatably disposed therein which are connected respectively to rotatable shafts of the motors 40, 41, 42. The pulleys 50a, 50b, 50c have respective couplings.

Wires 52, 53, 54 are wound around the pulleys 50a, 50b, 50c, respectively, and extend through a space 48a (see FIG. 5) in the hollow joint shaft 48 to the distal-end working unit 12. The wires 52, 53, 54 may be of the same type and diameter.

The working unit 16 can be separated from the operating unit 14 by a certain action made on the actuator block 30, so that the working unit 16 can be cleaned, sterilized, or serviced for maintenance. The working unit 16 may be replaced with another type of working unit. Depending on the nature of a surgical procedure to be carried out using the manipulator 10, a working unit 16 whose joint shaft 48 has a different length or whose distal-end working unit 12 has a different mechanism may be mounted on the operating unit 14.

The working unit 16 is detachably mounted on the operating unit 14. When the working unit 16 is mounted on the operating unit 14, the rotatable shafts 40a, 41a, 42a of the motors 40, 41, 42 are fitted into center holes of the pulleys 50a, 50b, 50c. Specifically, the lower ends of the pulleys 50a, 50b, 50c have respective criss-cross joint protrusions thereon, and the upper ends of the rotatable shafts 40a, 41a, 42a have respective criss-cross joint recesses defined therein. When the working unit 16 is mounted on the operating unit 14, the criss-cross joint protrusions on the lower ends of the pulleys 50a, 50b, 50c are fitted in the respective joint recesses in the upper ends of the rotatable shafts 40a, 41a, 42a, for reliably transferring rotational forces from the motors 40, 41, 42 to the pulleys 50a, 50b, 50c. The joint protrusions and the joint recesses are not limited to the criss-cross shape, but may have other interfitting shapes.

The connector 15 has an ID holder 104 for holding an ID capable of individually identifying the working unit 16.

The ID holder 104 may be a wireless ID holder such as RFID (Radio Frequency Identification) holder, a non-contact detection ID holder such as an optical ID holder which may be a bar code, a matrix two-dimensional code, or the like, or a contact detection ID holder such as a sequence of small protrusions or the like.

If a writable recording medium such as an RFID recording medium is used as the ID holder 104, then it may store various items of inherent information of the working unit 16, such as time stamps including the manufacturing date, the date of first use, the date of last use, and the date by which the working unit 16 needs to be serviced for maintenance, the serial number of the working unit 16, the number of times that the working unit 16 can be used, the corrected phase value (corrective origin value), etc. These items of inherent information of the working unit 16 may be read by the controller 514 and displayed on an operational state display unit 530 (see FIG. 1) of the controller 514, or may be judged by the controller 514 as a basis for giving a caution or a warning.

The ID held by the ID holder 104 is of a value for identifying each of the working units 16a through 16d.

The ID holder 104 does not need to be directly electrically energized, and hence the connector 15 and the working unit 16 have no electric contacts. Therefore, when dismounted from the operating unit 14, the working unit 16 can easily be cleaned or sterilized. Specifically, all the electric components including the motors, the switches, and the sensors are placed in the operating unit 14, and only mechanical components including the joint shaft 48 and the distal-end working unit 12 are provided as the working unit 16, so that the working unit 16 can efficiently be cleaned. It is preferable that the working unit 16 and the operating unit 14 be separable from each other because they will be smeared differently with different materials in use and will be differently cleaned and serviced for maintenance.

The operating unit 14 has an ID relay unit 106 for reading information held by the ID holder 104 and supplying the read information to the controller 514. The ID relay unit 106 may comprise an RFID transmitting and receiving circuit, a photocoupler, or the like.

If the ID holder 104 and the ID relay unit 106 are of a magnetic, optical, or radio-wave data transmission design, then the ID can be transferred from the ID holder 104 to the ID relay unit 106 in a non-contact manner. Therefore, the ID holder 104 and the ID relay unit 106 can be highly durable, smeared less, and cleaned with ease.

The actuator block 30 has a pair of levers 206 pivotally mounted on respective outer side surfaces thereof. The levers 206 have respective wedges 206a on upper inner surfaces thereof which engage respective engaging pieces 200 on outer side surfaces of the connector 15 when the connector 15 is mounted on the actuator block 30. The levers 206 are normally biased by an elastic member to hold the wedges 206a in locking engagement with the engaging pieces 200. For removing the connector 15 from the operating unit 14, the operator pushes the lower portions of the levers 206 to tilt the upper portions thereof outwardly, releasing the wedges 206a out of engagement with the engaging pieces 200. The connector 15 can now be pulled upwardly in the Y1 direction and detached from the operating unit 14. The actuator block 30 has three alignment pins 212 projecting upwardly from its upper surface. The connector 15 has three fitting holes 202 defined therein and opening downwardly. When the alignment pins 212 are fitted respectively in the fitting holes 202, the connector 15 is stably supported on the actuator block 30. For installing the connector 15 on the operating unit 14, the alignment pins 212 are positioned in alignment with the respective fitting holes 202, and then the connector 15 is pushed downwardly in the Y2 direction toward the actuator block 30. As the connector 15 is displaced toward the actuator block 30, the upper portions of the levers 206 are spread outwardly by the engaging pieces 200. When the wedges 206a move past the engaging pieces 200, the levers 206 snap back under the elasticity of the elastic member, bringing the wedges 206a into locking engagement with the engaging pieces 200. The connector 15 is now locked in place on the actuator block 30.

A working unit detecting unit 107 for detecting whether the connector 15 is placed on the actuator block 30 or not, is disposed on an upper surface 30b of the actuator block 30 at an end thereof in the Z2 direction. The working unit detecting unit 107 comprises a light emitter 107a and a light detector 107b that are positioned in confronting relation to each other. When a portion of the rear end of the connector 15 is inserted between the light emitter 107a and the light detector 107b, it blocks light emitted from the light emitter 107a toward the light detector 107b, thereby detecting the connector 15 mounted on the actuator block 30. The light emitter 107a and the light detector 107b confront each other in the X directions and are disposed closely to each other. The light emitter 107a may be an LED, for example, and the light detector 107b may be a photodiode, for example.

Figure 5:
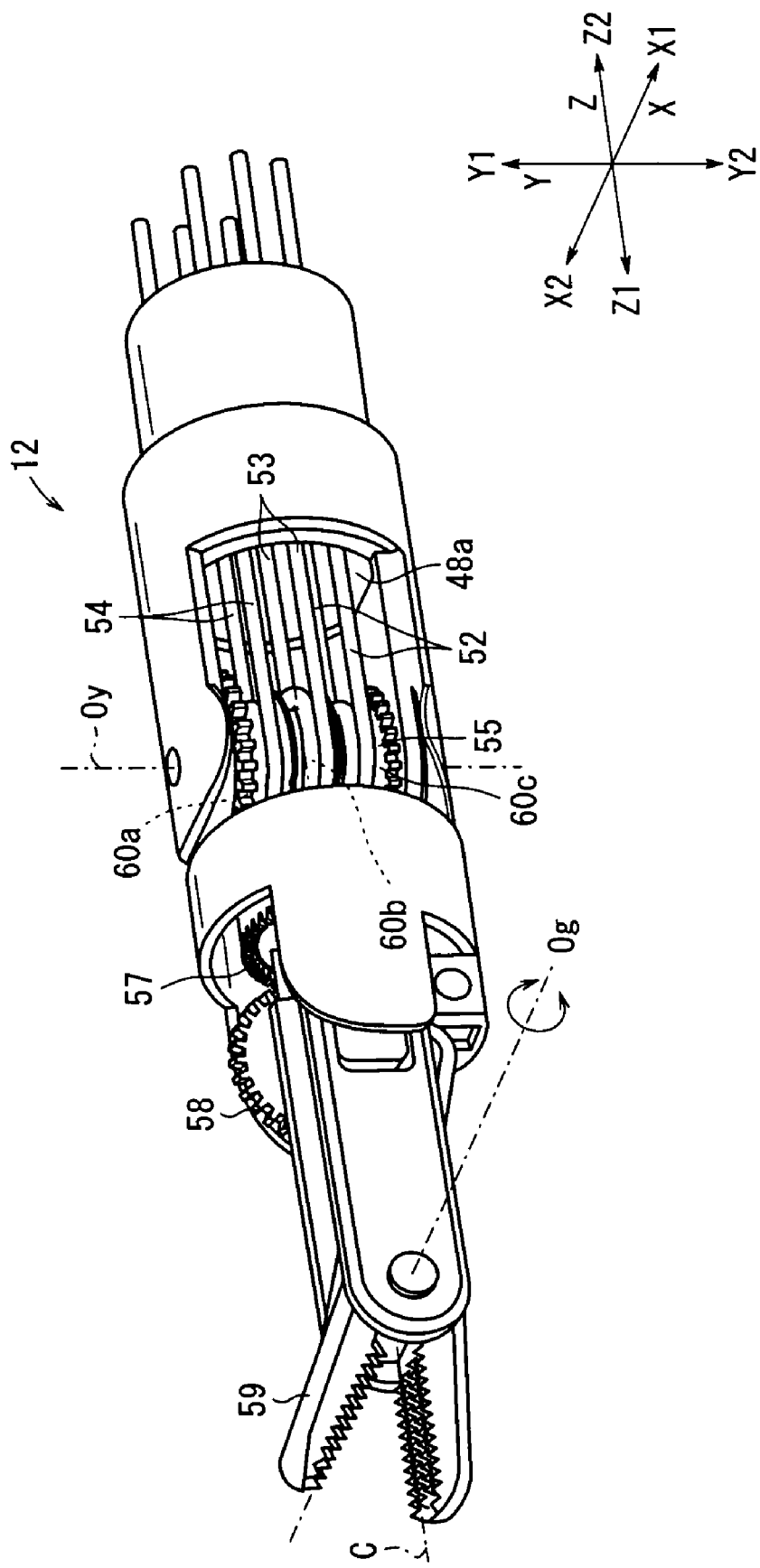
FIG. 5 is a perspective view of a distal-end working unit of the working unit.
Figure 6:
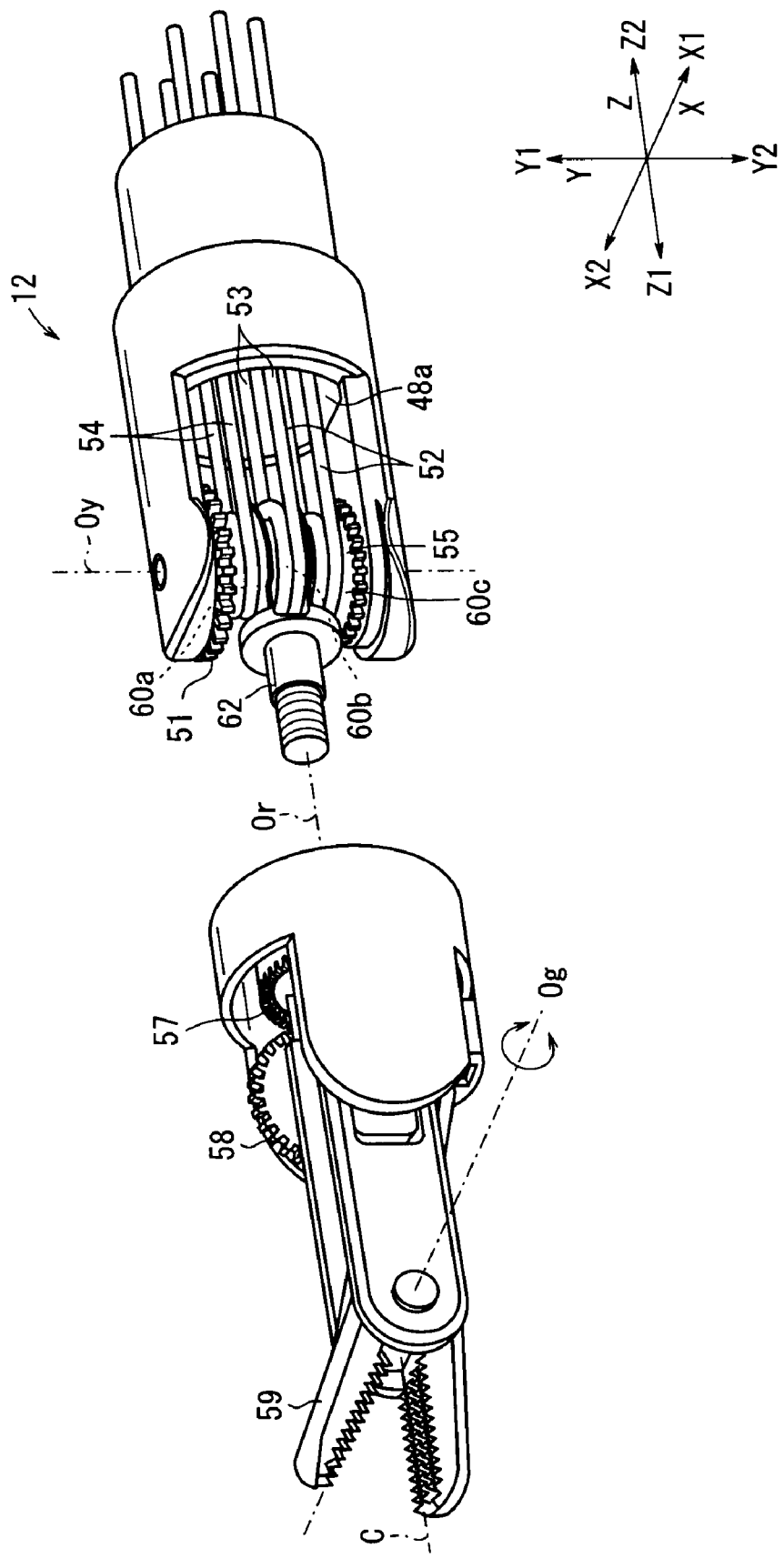
FIG. 6 is an exploded perspective view of the distal-end working unit.

As shown in FIGS. 5 and 6, the distal-end working unit 12 incorporates therein mechanisms of three degrees of freedom. These mechanisms include a mechanism (tilting mechanism, pivot axis) having a first degree of freedom for angularly moving a distal end portion that is positioned ahead of a first rotational axis Oy extending along the Y directions, in yawing directions about the first rotational axis Oy, a mechanism (rolling mechanism) having a second degree of freedom for angularly moving the distal end portion in rolling directions about a second rotational axis Or extending along the Z directions, and a mechanism having a third degree of freedom for opening and closing the gripper 59 on the distal end about a third rotational axis Og extending along the X directions.

The first rotational axis Oy of the mechanism having the first degree of freedom may be an axis about which the distal end portion is angularly movable, not parallel to an axis C that extends from the proximal to distal end of the joint shaft 48. The second rotational axis Or of the mechanism having the second degree of freedom may be an axis along which the distal end (i.e., the gripper 59) of the distal-end working unit 12 extends and about which the gripper 59 is rotatable in the rolling directions.

The distal-end working unit 12 is actuated by the wires 52, 53, 54 which are wound around corresponding tubular members 60c, 60b, 60a rotatably supported in the distal end of the joint shaft 48.

When the wires 52, 54 are moved, gears 51, 55 are rotated, causing a face gear, not shown, to rotate the gripper 59 in the rolling directions. When the wire 54 is moved, the gear 51 is rotated, causing a face gear 57 and a gear 58 to open and close the gripper 59. When the wires 52, 53, 54 are moved, a support bar 62 is angularly moved to turn the gripper 59 in the yawing directions.

The controller 514 will be described in detail below with reference to FIGS. 7 through 9.

Figure 7:
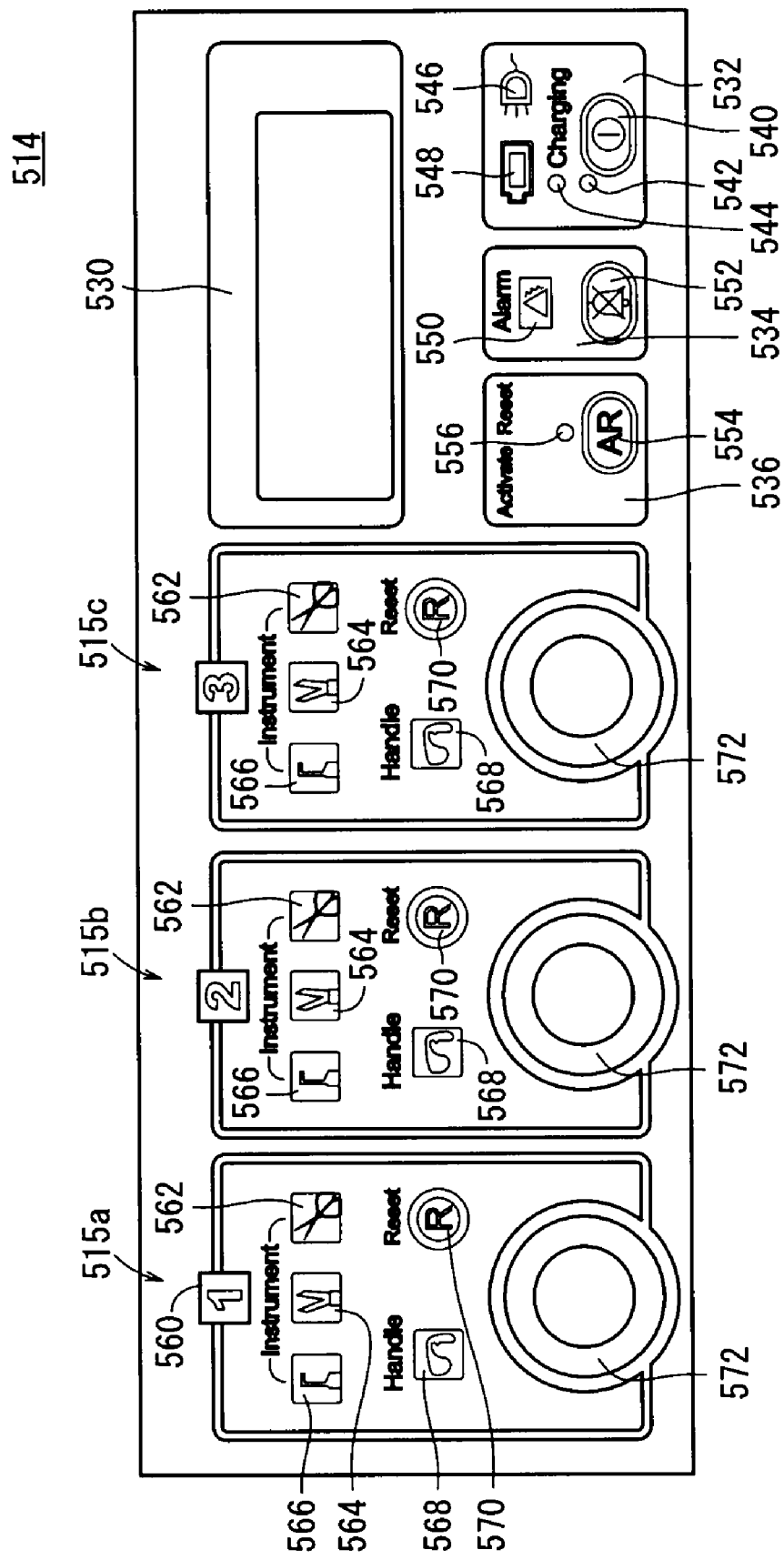
FIG. 7 is a front elevational view of a controller of the medical manipulator system according to the embodiment of the present invention.

As shown in FIG. 7, the controller 514 has, on its front surface, the operational state display unit 530, a power supply information display unit 532, an alarm unit 534, an activation resetting unit 536, the first port 515a, the second port 515b, and the third port 515c.

The operational state display unit 530 includes a liquid crystal display panel for displaying operational states of the manipulator 10 and commands therefor for the surgeon and surgical assistants to easily confirm how the manipulator 10 is being controlled.

The power supply information display unit 532 includes a power supply switch 540, a power supply lamp 542, a charging lamp 544, an external power supply warning lamp 546, and a battery charging indicator lamp 548.

The power supply switch 540 is a switch for turning on and off a power supply 112 of the manipulator system 500. When the power supply 112 of the manipulator system 500 is turned on, the power supply lamp 542 is energized, and when the power supply 112 of the manipulator system 500 is turned off, the power supply lamp 542 is de-energized. The charging lamp 544 is energized when a battery 112a (see FIG. 9) of the power supply 112 is being charged. The external power supply warning lamp 546 is energized when an external power supply 119 does not supply electric power to the manipulator system 500. The battery charging indicator lamp 548 displays a variable level of remaining electric power stored in the battery 112a by changing either the number of energized lamp elements thereof or the color of light emitted thereby.

The alarm unit 534 includes an alarm lamp 550 and an alarm sound stop switch 552. The alarm lamp 550 is a lamp which is energized when the controller 514 produces an alarm. The alarm lamp 550 is energized in synchronism with the sound of an alarm buzzer in the controller 514. The alarm sound stop switch 552 is a switch which is pressed by the operator when the operator wants to stop the sound of the alarm buzzer.

The activation resetting unit 536 includes an activation resetting switch (first resetting switch) 554 and a resetting indicator lamp 556. The resetting indicator lamp 556 is energized at times to carry out the resetting process for forcibly returning the motors 40, 41, 42 of the manipulator 10 to the origin. The activation resetting switch 554 is a switch which is pressed by the operator to indicate a first cycle of the resetting process while the resetting indicator lamp 556 is being energized.

The first port 515a includes the port number lamp 560, three working unit type lamps 562, 564, 566, an operating unit connection confirmation lamp 568, a resetting switch (second resetting switch) 570, and a receptacle connector 572. The connector 520, referred to above, for connecting the manipulator 10 to the controller 514 is connected to the receptacle connector 572.

The port number lamp 560 is printed with number "1". When the corresponding manipulator 10 is in the operation mode, the port number lamp 560 is energized to emit green light, for example, and when the corresponding manipulator 10 is in the stop mode, the port number lamp 560 is de-energized. When the corresponding manipulator 10 is in the automatic origin return process and the resetting process (automatic mode), the port number lamp 560 emits blinking light. When the corresponding manipulator 10 generates an alarm, the port number lamp 560 emits blinking red light. The port number lamp 560 changes its energized states in synchronism with the LED 29.

One of the working unit type lamps 562, 564, 566 is energized depending on the type of the working unit 16 that is connected to the operating unit 14, indicating the type of the connected working unit 16. Specifically, the working unit type lamp 562 is energized if the connected working unit 16 is scissors. The working unit type lamp 564 is energized if the connected working unit 16 is a gripper. The working unit type lamp 566 is energized if the connected working unit 16 is an electrosurgical knife.

The operating unit connection confirmation lamp 568 is energized when the connector 520 is properly connected to the receptacle connector 572. The resetting switch 570 is a switch combined with a lamp. When the resetting process for the corresponding manipulator 10 is required, the lamp of the resetting switch 570 is energized after the operator presses the activation resetting switch 554. When the operator presses the resetting switch 570 after the lamp of the resetting switch 570 is energized, the motors 40, 41, 42 of the corresponding manipulator 10 are automatically reset by the controller 514. While the motors 40, 41, 42 are being reset, the LED 29 and the port number lamp 560 blink, indicating that the manipulator 10 is in the automatic mode.

The second port 515b and the third port 515c are essentially the same as the first port 515a except that the port number lamps 560 of the second port 515b and the third port 515c are printed with number "2" and number "3", respectively. Therefore, the components of the second port 515b and the third port 515c which are identical to those of the first port 515a, are denoted by identical reference characters, and will not be described in detail below.

The first port 515a, the second port 515b, and the third port 515c are surrounded by respective frames in different colors (e.g., green, yellow, and blue), so that they can easily be distinguished visually.

The switches and the lamps of the controller 514 bear symbol marks, letters, or abbreviations indicative of their functions. The switches and the lamps of the controller 514 are in the form of membranes that are easy to handle and highly environmentally resistant.

A process for forcibly returning the motors 40, 41, 42 of the manipulator 10 to the origin and resetting the positional information of the motors 40, 41, 42 in the controller 514 will be described below with reference to a processing sequence shown in FIG. 8. The resetting process for resetting the positional information of the motors 40, 41, 42 is initiated by the operator when the working unit 16 is removed from the operating unit 14 while the motors 40, 41, 42 are not returned to the origin, or when the connector 520 is disconnected from the receptacle connector 572 while the motors 40, 41, 42 are not returned to the origin. Specifically, the resetting process is initiated when the operator presses the activation resetting switch 554 and the resetting switch 570 according to a predetermined procedure. The processing sequence shown in FIG. 8 deals with the resetting process for the manipulator 10a that is connected to the first port 515a of the controller 514. The processing sequence shown in FIG. 8 is basically carried out under the control of the controller 514.

Figure 8:
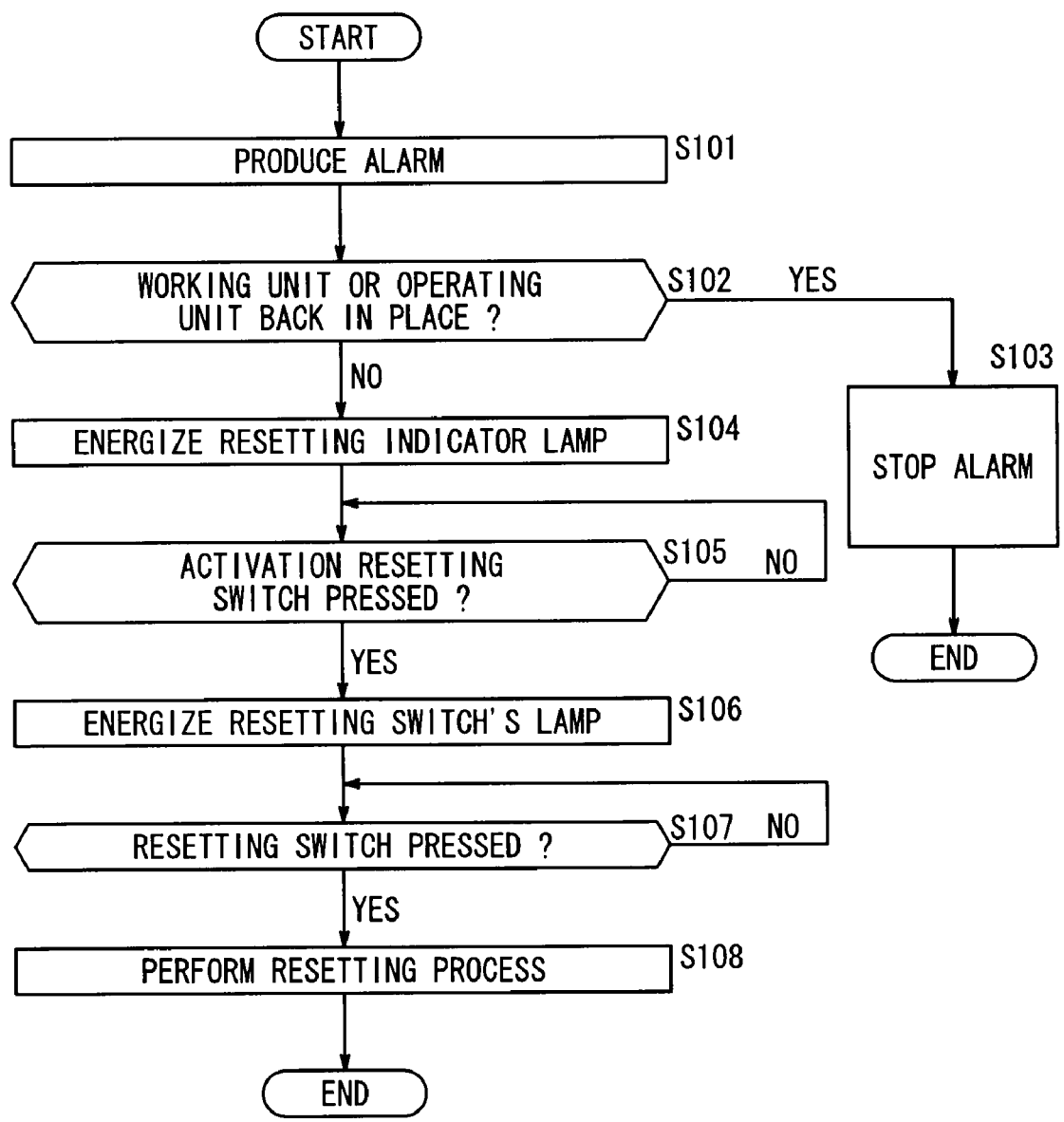
FIG. 8 is a flowchart of a processing sequence including the generation of an alarm and actions made in response to the alarm.

When the working unit 16 is removed from the operating unit 14 while at least one of the motors 40, 41, 42 of the manipulator 10a connected to the first port 515a is not returned to the origin, or when the connector 520 is disconnected from the receptacle connector 572 while at least one of the motors 40, 41, 42 is not returned to the origin, i.e., when the working unit 16 is removed from the operating unit 14 of the manipulator 10a, or when the connector 520 corresponding to the manipulator 10a is disconnected from the receptacle connector 572, the controller 514 produces an alarm in step S101 shown in FIG. 8. Specifically, the controller 514 energizes the alarm lamp 550, changes the port number lamp 560 from green light lighting to red light blinking, and turns on the alarm buzzer.

The controller 514 determines whether the working unit 16 is removed from the operating unit 14 or not based on the signal from the working unit detecting unit 107. The controller 514 determines whether the connector 520 is disconnected from the receptacle connector 572 or not based on a change in an operation command input from the composite input unit 34.

The controller 514 displays a message "RETURN WORKING UNIT TO PORT 1" or a message "RETURN CONNECTOR TO PORT 1", for example, on the operational state display unit 530. The operator then makes a corresponding action based on the displayed message. Specifically, if the connector 520 is connected to the receptacle connector 572, but the working unit 16 is removed from the operating unit 14, then the operator reinstalls the removed working unit 16 on the operating unit 14. If the connector 520 is disconnected from the receptacle connector 572, then the operator connects the connector 520 again to the receptacle connector 572. Thereafter, the operator makes a predetermined action to return the motors 40, 41, 42 to the origin.

If the working unit 16 is installed again on the operating unit 14 or the connector 520 is connected again to the receptacle connector 572 in step S102, then the controller stops the alarm in step S103. Specifically, the controller 514 de-energizes the alarm lamp 550, stops the alarm buzzer, and changes the emitted light of the port number lamp 560 and the LED 29 to green light. The controller 514 turns off the displayed message on the operational state display unit 530, or changes the displayed message on the operational state display unit 530 to a message indicating that the working unit 16 is reinstalled on the operating unit 14 or the connector 520 is connected again to the receptacle connector 572.

If the controller 514 judges that the working unit 16 cannot be reinstalled on the operating unit 14 or the connector 520 cannot be connected again to the receptacle connector 572 for some reasons, e.g., the working unit 16 or the operating unit 14 is suffering a failure and cannot be used, then control goes from step S102 to step S104.

In step S104, the controller 514 displays a message "PRESS "AR" SWITCH IF WORKING UNIT OR CONNECTOR CANNOT BE MOUNTED AGAIN" on the operational state display unit 530, and energizes the resetting indicator lamp 556 to indicate that the activation resetting switch 554 is valid.

In step S105, the controller 514 confirms whether the activation resetting switch 554 is pressed or not. If the activation resetting switch 554 is pressed, then control goes to step S106. If the activation resetting switch 554 is not pressed, then control waits until the activation resetting switch 554 is pressed. The resetting switch 570 is not valid until the activation resetting switch 554 is pressed. After the activation resetting switch 554 is pressed, the controller 514 de-energizes the resetting indicator lamp 556.

In step S106, the controller 514 energizes the lamp of the resetting switch 570 of the first port 515a, indicating that the resetting switch 570 is valid. At this time, the lamps of the resetting switches 570 of the second and third ports 515b, 515c are de-energized, so that the operator can easily understand that only the resetting switch 570 of the first port 515a is valid.

In step S107, the controller 514 confirms whether the resetting switch 570 of the first port 515a is pressed or not. If the resetting switch 570 is pressed, control goes to step S108. If the resetting switch 570 is not pressed, control waits until the resetting switch 570 is pressed.

If the working unit 16 is mounted or the connector 520 is connected while control is waiting in step S107 or S105, then the controller 514 may de-energize the resetting indicator lamp 556 and then cancel the alarm in step S103 according to an interrupt routine, not shown.

In step S108, the controller 514 performs the resetting process. Specifically, if the connector 520 is connected to the first port 515a, then the controller 514 forcibly returns the motors 40, 41, 42 to the origin regardless of whether the working unit 16 is mounted on the operating unit 14 or not. By thus forcibly returning the motors 40, 41, 42 to the origin, the controller 514 can appropriately control another working unit 16 when it is installed on the operating unit 14. After the resetting process, the controller 514 de-energizes the lamp of the resetting switch 570.

If the connector 520 is disconnected from the first port 515a, the controller 514 resets the positional information (the internal signals indicative of angles of the motors 40, 41, 42), stored in the controller 514, of the motors 40, 41, 42 of the operating unit 14 associated with the first port 515a, to the origin. The positional information may be saved in a certain storage area before being reset. By thus forcibly returning the positional information of the motors 40, 41, 42 to the origin, the controller 514 can appropriately control another operating unit 14 when it is connected to the controller 514.

After the resetting process, the controller 514 displays the end of the resetting process on the operational state display unit 530. The processing sequence shown in FIG. 8 is carried out at the time of a non-origin mount/removal error at Y15 (see FIG. 10) as described later.

In the medical manipulator system 500 according to the present embodiment, as described above, when the activation resetting switch 554 and the resetting switch 570 are operated according to a predetermined procedure (i.e., the resetting indicator lamp 556 is energized, the activation resetting switch 554 is pressed, the lamp of the resetting switch 570 is energized, and thereafter the resetting switch 570 is pressed), the resetting process is carried out to return the actuators to the origin. Accordingly, the resetting process is not activated carelessly. The procedure for operating the activation resetting switch 554 and the resetting switch 570 is not limited to the above two-stage procedure, but may be any of other procedures. For example, the procedure for operating the activation resetting switch 554 and the resetting switch 570 may include a process of simultaneously pressing the activation resetting switch 554 and the resetting switch 570.

In the above description, the working unit 16 is removed from the operating unit 14 of the manipulator 10a or the connector 520 is disconnected from the controller 514. However, the working unit 16 may be removed from the operating unit 14 of at least one of the manipulators 10a through 10c or the connector 520 corresponding to at least one of the manipulators 10a through 10c may be disconnected from the controller 514.

The energized resetting indicator lamp 556 is de-energized when an error about the first through third ports 515a through 515c is eliminated. The alarm lamp 550 is also de-energized in the same way.

The controller 514 has the three resetting switches 570, so that the manipulators 10a through 10c (see FIG. 1) can individually be reset. As the controller 514 has only one activation resetting switch 554, it is prevented from having an unduly large number of switches, is structurally simple, and can be operated easily.

Since the activation resetting switch 554 and the resetting switches 570 are provided on the controller 514, the manipulator 10 is prevented from being unduly structurally complex, is simple and lightweight, and can be operated easily.

The controller 514 has a function to detect errors about the individual three manipulators. If an error occurs in the first port 515a, for example, the port number lamp 560 representing number "1" emits blinking red light. When the activation resetting switch 554 is pressed, the lamp of the resetting switch 570 of the first port 515a, in which an error occurs, emits light. Thus, the controller 514 is simple to operate and is prevented from being operated in error.

If an error occurs in the manipulator 10a, then the second port 515b and the third port 515c do not display alarm regardless of whether the connector 520 is connected or not. Consequently, the operator finds it easy to recognize that the alarm has been produced with respect to the manipulator 10a connected to the first port 515a.

Internal details of the controller 514 will be described below with reference to FIG. 9. In FIG. 9, only components related to the first port 515a are illustrated for the sake of brevity, and those related to the second and third ports 515b, 515c are omitted from illustration. Some (e.g., a processor 110, etc.) of the components related to the second and third ports 515b, 515c are shared by the first port 515a, and other components (e.g., a driver 116, etc.) related to the second and third ports 515b, 515c are independent. In FIG. 9, the components on the front surface (see FIG. 7) of the controller 514 are omitted from illustration.

Figure 9:
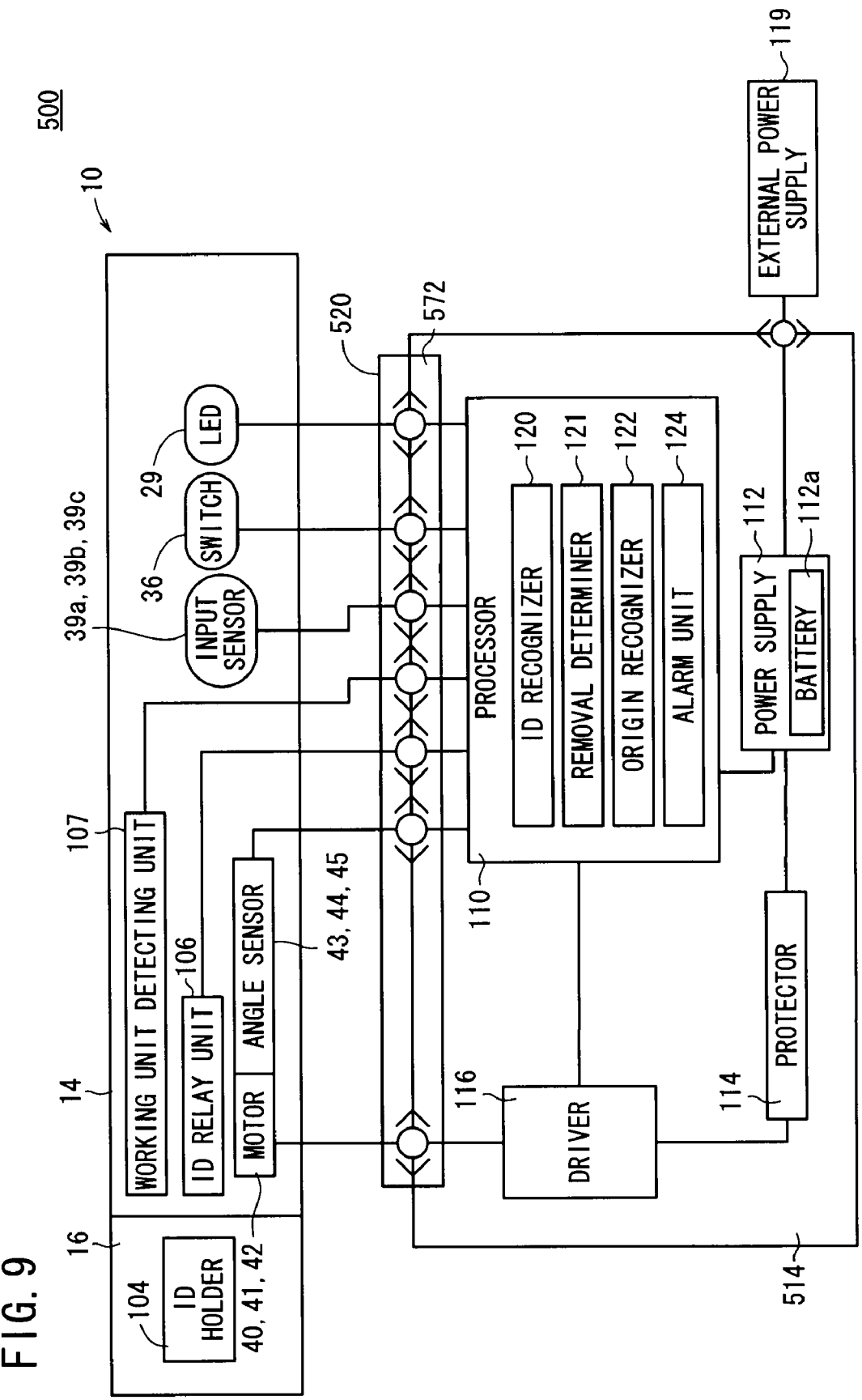
FIG. 9 is a block diagram of the controller.

As shown in FIG. 9, the controller 514 includes the processor 110, the power supply 112, a protector 114, and a driver 116. The power supply 112 regulates electric power supplied from the external power supply 119 and supplies the regulated electric power to various components in the controller 514, charges the battery 112a, and automatically switches to the battery 112a in the event that no electric power is supplied from the external power supply 119. The power supply 112 thus operates as an uninterruptable power supply. The battery 112a is connected parallel to a transformer-rectifier assembly in the power supply 112.

The protector 114 shuts off electric power supplied to the manipulator 10 based on various items of information including processing period information, driver information, stop commands, etc. of the processor 110. When the protector 114 shuts off electric power supplied to the driver 116, the manipulator 10 immediately stops its operation.

The processor 110 is electrically connected to the angle sensors 43, 44, 45, the input sensors 39a, 39b, 39c, and the switch 36. Based on the signals from these sensors and switch, the processor 110 determines how to operate the manipulator 10, supplies a predetermined command signal to the driver 116, and controls the operational state display unit 530 to display a certain operational state. The processor 110 is also electrically connected to the LED 29 to control the energized state thereof. The processor 110 is further electrically connected to the operational state display unit 530, the power supply information display unit 532, the alarm unit 534, the activation resetting unit 536, the first port 515a, the second port 515b, and the third port 515c on the front surface (see FIG. 7) of the controller 514 for controlling them. The processor 110 comprises a CPU, a ROM, a RAM, etc., and performs a certain software process by reading and executing a program.

The driver 116 is electrically connected to the motors 40, 41, 42, and energizes the motors 40, 41, 42 based on commands from the processor 110. A drive system for the motors 40, 41, 42 determines operational angle command values for the distal-end working unit 12 based on the signals from the input sensors 39a, 39b, 39c, determines the differences between the operational angle command values and the angle signals from the angle sensors 43, 44, 45, performs a predetermined compensating process based on the differences, and supplies command signals to the driver 116. Therefore, the drive system for the motors 40, 41, 42 is of a closed loop.

The processor 110 includes an ID recognizer 120, a removal determiner 121, an origin recognizer 122, and a warning unit 124. The ID recognizer 120 recognizes the ID of the ID holder 104. The removal determiner 121 determines the identity of the working unit 16 as it is removed from and installed on the operating unit 14 based on the ID recognized by the ID recognizer 120.

The processor 110 determines conditions based on signals from the ID recognizer 120 and the origin recognizer 122 and other signals from the operating unit 14, and stops supplying electric power to the driver 116 under certain conditions to de-energize the motors 40, 41, 42. Alternatively, the processor 110 may operate a relay to disconnect the driver from the connector 520 to de-energize the motors 40, 41, 42.

A certain voltage is applied to the input sensors 39a, 39b, 39c (potentiometers or the like) that are associated with the trigger lever 32 and the composite input unit 34 (see FIG. 1), and a certain range is established as an operating range with respect to the voltage. If a voltage from the input sensors 39a, 39b, 39c falls out of the operating range, then the controller 514 recognizes that the operating unit 14 is removed. Thus, the trigger lever 32 and the composite input unit 34 may be used as both an input means for inputting operation variables and a removal recognizing means for recognizing the removal of the operating unit 14.

The origin recognizer 122 recognizes whether the distal-end working unit 12 is at the origin or not based on the signals from the angle sensors 43, 44, 45. When it is judged that the distal-end working unit 12 is not at the origin based on the signal from the origin recognizer 122 and it is judged that the working unit 16 is removed from the operating unit 14 based on the signal from the ID relay unit 106, the warning unit 124 produces a removal warning.

While the warning unit 124 is producing the removal warning, the warning unit 124 monitors the ID from the ID recognizer 120. When the warning unit 124 recognizes that any one of the working units 16a through 16d is connected again and the obtained ID is equal to the ID recognized prior to the removal, the warning unit 124 cancels the removal warning. When the obtained ID is not equal to the ID recognized prior to the removal, the warning unit 124 produces a connection error warning, and displays a corresponding warning message on the operational state display unit 530.

The removal warning and the connection error warning may be given as sound warnings produced by a sound/speech means or as warning messages displayed on the operational state display unit 530. The removal warning and the connection error warning should preferably be easily distinguishable from each other. If the removal warning and the connection error warning are given as sound warnings produced by the sound/speech means, then they may be buzzer sounds produced at different intervals or frequencies.

If the ID relay unit 106 and the ID recognizer 120 judge that the working unit 16 is removed, or if the origin recognizer 122 judges that the distal-end working unit 12 is at the origin, then the protector 114 operates to stop supplying electric power to the driver 116.

The removal and installation of the working unit 16 in the manipulator system 500 will be described below.

Figure 10:
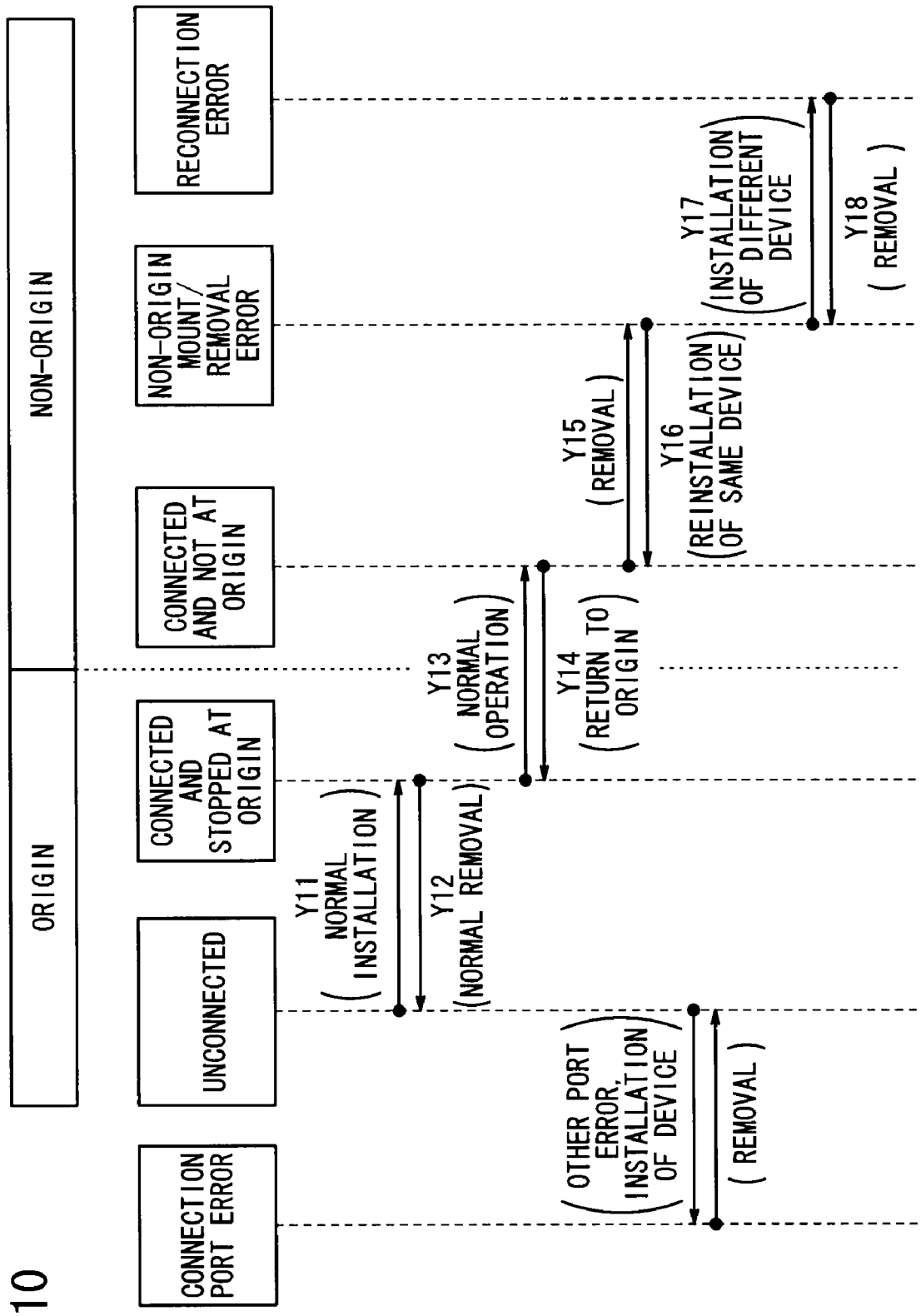
FIG. 10 is a diagram showing general operational details of the medical manipulator system at the time the working unit is installed and removed.

In FIG. 10, it is assumed that the manipulator 10a including the operating unit 14a and the working unit 16a is initially connected to the controller 514. The operator, i.e., the surgeon, performs a surgical procedure using the manipulator 10a. The manipulator 10a is in a normal operational state (Y13) in which the working unit 16a operates according to commands from the operating unit 14a.

For removing the working unit 16a and replacing it with one of the other working units 16b through 16d, the axis positions of the motors 40, 41, 42 of the operating unit 14a are returned to the origin (Y14). After the origin recognizer 122 confirms that the motors 40, 41, 42 have stopped at the origin, the operator removes the working unit 16a from the operating unit 14a (Y12) and replaces the working unit 16a with a desired one of the other working units 16b through 16d (Y11). The operator can confirm the operating unit 14a being returned to the origin when the LED 29 on the operating unit 14 and the port number lamp 560 on the front surface of the controller 514 are de-energized.

If the operator removes the working unit 16a from the operating unit 14a (Y15) when the motors 40, 41, 42 of the operating unit 14a are not at the origin, then the origin recognizer 122 and the ID recognizer 120 recognize such a state. This state is defined as a non-origin mount/removal error. The warning unit 124 operates to energize the alarm lamp 550, to produce an alarm sound, and to display a predetermined warning message on the operational state display unit 530, letting the operator recognize the non-origin mount/removal error (see FIG. 8).

For returning from the non-origin mount/removal error to the normal state, the operator reinstalls the removed working unit 16a on the operating unit 14a (Y16). The operator can continue operating the manipulator 10a from the time it removed the working unit 16a from the operating unit 14a. The non-origin mount/removal error and the removal warning are now canceled. The axis positions of the motors 40, 41, 42 and the pulleys 50a, 50b, 50c are returned to the origin and stopped, whereupon the manipulator 10a is in a state identical to Y14. The operator can now remove the working unit 16a and replace it with a desired one of the working units 16b through 16d.

If one of the working units 16b through 16d, which is different from the working unit 16a, is connected in the state of the non-origin mount/removal error (Y17), then the origin recognizer 122 and the ID recognizer 120 recognize such a state. This state is defined as a reconnection error. The warning unit 124 operates to produce a connection error warning, letting the operator recognize the reconnection error.

When the operator removes the connected one of the working units 16b through 16d (Y18), the reconnection error and the connection error warning are canceled, and the manipulator 10a returns to the state of the non-origin mount/removal error. The removal warning is produced again.

Operation of the manipulator system 500 will be described below with reference to a flowchart shown in FIG. 11.

The manipulator system 500 operates under the general control of the processor 110 of the controller 514, and basically performs an operation sequence according to the flowchart shown in FIG. 11. The operation sequence according to the flowchart shown in FIG. 11 is repeatedly carried out in predetermined control periods. It is assumed that the operation sequence is performed in the order of step numbers unless otherwise indicated.

In step S11 shown in FIG. 11, the processor 110 reads output signals from angle detectors in the operating unit 14 and the angle sensors 43, 44, 45 for the motors 40, 41, 42.

In step S12, the processor 110 recognizes input signals from the command input means, the switch 36, and the like.

In step S13, the processor 110 determines a control mode for the manipulator 10 based on the input signals recognized by the processor 110.

In step S14, the processor 110 determines an operating process and control target values for the motors 40, 41, 42 according to the determined control mode. The control mode refers to an automatic control mode for automatically operating the working unit 16 according to a predetermined pattern or a master-slave control mode for operating the working unit 16a based on the operation of the operating unit 14. The operating process refers to an accelerating process, a decelerating process, an equal-speed process, a stopping process, etc. for operating the working unit 16 reliably and smoothly upon switching from one control mode to another.

In step S15, the processor 110 calculates motor output signals from the control target values and the angle signals from the angle sensors 43, 44, 45 according to a control process such as a PID control process, and outputs the calculated motor output signals to the driver 116.

In step S16, the processor 110 compares various defined conditions and the angle signals from the angle sensors 43, 44, 45 and the like with each other, and determines the state of the manipulator 10.

In step S17, the processor 110 outputs signals to the lamps on the controller 514 based on the determined state of the manipulator 10.

In the above embodiment, the manipulator system 500 has three connection ports. However, the manipulator system 500 may have four or more connection ports because some laparoscopic surgical procedures need four or more manipulators and some laparoscopic surgical procedures should preferably keep additional manipulators for use as backup manipulators or for use in next surgical techniques even if only two manipulators are normally used at a time.

As two or more manipulators are controlled by the single controller 514, some components, e.g., the processor 110, of the controller 514 are shared for reduced power consumption.

Although a certain preferred embodiment of the present invention has been shown and described in detail, it should be understood that various changes and modifications may be made therein without departing from the scope of the appended claims.

What is claimed is:

1. A medical manipulator system comprising:
a manipulator;
a controller connected to the manipulator; and
a first resetting switch and a second resetting switch;
the manipulator comprising:
an operating unit having an actuator, a grip handle for being gripped by a human hand, and an input unit for inputting an operation command;
a working unit removably mounted on the actuator and having a shaft and a distal-end working unit mounted on a distal end of the shaft, the distal-end working unit being angularly movable about a pivot axis not parallel to an axis of the shaft in response to operation of the actuator; and
a working unit detecting unit for supplying the controller with a signal indicating whether the working unit is present on the operating unit or not;
wherein when the working unit is removed from the operating unit and when the actuator is not at an origin, the controller produces a warning, and performs a resetting process to return the actuator to the origin if both of the first resetting switch and the second resetting switch are operated according to a predetermined procedure.

2. A medical manipulator system comprising:
a manipulator;
a controller connected to the manipulator; and
a first resetting switch and a second resetting switch;
the manipulator comprising:
an operating unit having an actuator, a grip handle for being gripped by a human hand, and an input unit for inputting an operation command, the operating unit being connected to the controller by a connector; and
a working unit removably mounted on the actuator and having a shaft and a distal-end working unit mounted on a distal end of the shaft, the distal-end working unit being angularly movable about a pivot axis not parallel to an axis of the shaft in response to operation of the actuator;
wherein the controller detects whether the connector is connected or disconnected based on a change in the operation command, and when the connector is disconnected and when the actuator is not at an origin, the controller produces a warning, and performs a resetting process to return an internal signal representing an angle of the actuator to the origin if both of the first resetting switch and the second resetting switch are operated according to a predetermined procedure.

3. A medical manipulator system according to claim 1, wherein the controller is capable of controlling N manipulators, the first resetting switch comprises a single resetting switch shared by the N manipulators, and the second resetting switch comprises N resetting switches corresponding respectively to the N manipulators.

4. A medical manipulator system according to claim 1, wherein the first resetting switch and the second resetting switch are provided in the controller.

5. A medical manipulator system according to claim 1, wherein the second resetting switch has a light-emitting element, and
the controller has a function to detect whether the working unit is mounted or removed individually with respect to the N manipulators and to detect an angle of the actuator, and wherein when the first resetting switch is pressed, the controller emits light from the light-emitting element of the second resetting switch corresponding to the manipulator with the working unit removed when the actuator is not at the origin, and the controller resets the manipulator after the second resetting switch whose light-emitting element is emitting light is pressed.

6. A medical manipulator system according to claim 2, wherein the second resetting switch has a light-emitting element, and
the controller has a function to detect whether the connector is connected or disconnected individually with respect to the N manipulators and to detect an angle of the actuator, and wherein when the first resetting switch is pressed, the controller emits light from the light-emitting element of the second resetting switch corresponding to the manipulator with the connector disconnected when the actuator is not at the origin, and the controller resets the manipulator after the second resetting switch whose light-emitting element is emitting light is pressed.

7. A medical manipulator system comprising:
a manipulator;
a controller connected to the manipulator; and
a first resetting switch and a second resetting switch;
the manipulator comprising:
an actuator block including an actuator;
a working unit removably mounted on the actuator block and having a shaft and a distal-end working unit mounted on a distal end of the shaft, the distal-end working unit being angularly movable about a pivot axis not parallel to an axis of the shaft in response to operation of the actuator; and
a working unit detecting unit for supplying the controller with a signal indicating whether the working unit is present on the operating unit or not;
wherein when the working unit is removed from the actuator block and when the actuator is not at an origin, the controller produces a warning, and performs a resetting process to return the actuator to the origin if both of the first resetting switch and the second resetting switch are operated according to a predetermined procedure.

* * * * *